(12) United States Patent
Beckstead et al.

(10) Patent No.: US 7,999,928 B2
(45) Date of Patent: Aug. 16, 2011

(54) METHOD AND SYSTEM FOR COMBINED RAMAN AND LIBS DETECTION

(75) Inventors: Jeffrey Beckstead, Valencia, PA (US);
Patrick J. Treado, Pittsburgh, PA (US);
Matthew Nelson, Harrison, PA (US)

(73) Assignee: ChemImage Corporation, Pittsburgh, PA (US)

(*) Notice: Subject to any disclaimer, the term of this patent is extended or adjusted under 35 U.S.C. 154(b) by 843 days.

(21) Appl. No.: 11/656,393

(22) Filed: Jan. 23, 2007

(65) Prior Publication Data
US 2010/0271629 A1    Oct. 28, 2010

Related U.S. Application Data

(60) Provisional application No. 60/761,235, filed on Jan. 23, 2006, provisional application No. 60/761,255, filed on Jan. 23, 2006, provisional application No. 60/761,256, filed on Jan. 23, 2006.

(51) Int. Cl.
*G01N 21/00* (2006.01)

(52) U.S. Cl. .......... 356/73; 356/73.1; 356/445; 356/301

(58) Field of Classification Search .......... 356/73, 356/73.1, 445, 446, 451, 301
See application file for complete search history.

(56) References Cited

U.S. PATENT DOCUMENTS

| | | | |
|---|---|---|---|
| 4,880,052 A | 11/1989 | Meyer, IV et al. | |
| 5,194,912 A | 3/1993 | Batchelder et al. | |
| 5,377,004 A | 12/1994 | Owen et al. | |
| 5,442,438 A | 8/1995 | Batchelder et al. | |
| 5,528,393 A | 6/1996 | Sharp et al. | |
| 5,539,517 A | 7/1996 | Cabib et al. | |
| 5,623,342 A | 4/1997 | Baldwin et al. | |
| 5,689,333 A | 11/1997 | Batchelder et al. | |
| 5,710,626 A | 1/1998 | O'Rourke et al. | |
| 5,862,273 A | 1/1999 | Pelletier | |
| 5,866,430 A | 2/1999 | Grow | |
| 5,901,261 A | 5/1999 | Wach | |
| 5,911,017 A | 6/1999 | Wach et al. | |
| 6,002,476 A | 12/1999 | Treado | |

(Continued)

FOREIGN PATENT DOCUMENTS
JP    9-121889 A    5/1997

OTHER PUBLICATIONS
Caetano, et al., "Evaluation of the Importance of Non-Linear Spectral Mixing in Coniferous Forests," SPIE vol. 3499, Sep. 1998, pp. 257-269.

(Continued)

*Primary Examiner* — Gregory J Toatley
*Assistant Examiner* — Iyabo S Alli
(74) *Attorney, Agent, or Firm* — Duane Morris LLP

(57) ABSTRACT

In one embodiment, the disclosure relates to a method for interrogating a sample by: illuminating a first region of the sample with a first illumination pattern to obtain a plurality of first sample photons; illuminating a second region of the sample with a second illumination pattern to obtain a plurality of second sample photons; processing the plurality of first sample photons to obtain a characteristic atomic emission of the first region and processing the plurality of second sample photons to obtain a Raman spectrum; and identifying the sample through at least one of the characteristic atomic emission of the first region or the Raman spectrum of the second region of the sample.

33 Claims, 7 Drawing Sheets

U.S. PATENT DOCUMENTS

| | | | |
|---|---|---|---|
| RE36,529 E | 1/2000 | Lewis et al. | |
| 6,717,668 B2 | 4/2004 | Treado et al. | |
| 6,734,962 B2 | 5/2004 | Treado et al. | |
| 6,954,667 B2 | 10/2005 | Treado et al. | |
| 6,965,793 B2 | 11/2005 | Treado et al. | |
| 6,992,809 B1 | 1/2006 | Wang et al. | |
| 7,362,489 B2 | 4/2008 | Wang et al. | |
| 7,474,685 B2* | 1/2009 | Kalayeh | 372/50.12 |
| 2008/0088837 A1* | 4/2008 | Gardner | 356/301 |

OTHER PUBLICATIONS

Rasmussen, et al., "Library Retrieval of Infrared Spectra Based on Detailed Intensity Information," Applied Spectroscopy, vol. 33, No. 4, Feb. 1979, pp. 371-376.

Guilment, et al., "Infrared Chemical Micro-imaging Assisted by Interactive Self-Modeling Multivariate Analysis," Applied Spectroscopy, vol. 48, No. 3, 1994, pp. 320-326.

Malinowski, Edmund R., "Factor Analysis in Chemistry," 1991, 2nd Edition, Published by John Wiley & Sons, Inc./ William H. Press, et al., pp. 32-82 and pp. 208-265.

Marquardt, et al., "Novel Probe for Laser-Induced Breakdown Spectroscopy and Raman Measurements Using an Imaging Optical Filter," Applied Spectroscopy, 1998, p. 1148-1153, vol. 52, No. 9.

Wiens, et al., "Development of a Prototype Laser-induced Breakdown Spectroscopy (LIBS) Instrument with Stand-off Raman Capabilities as part of the Mars Instrument Development Program," Lunar and Planetary Science Conference, XXXI, #1468, Houston, Texas, Mar. 13-17, 2000. (Available at: http://www.lpi.usra.edu/meetings/lpsc2000/pdf/1468.pdf), Last Accessed Sep. 23, 2008.

Wiens, et al., "Joint Analyses by Laser-induced Breakdown Spectroscopy (LIBS) and Raman Spectroscopy at Stand-off Distances," Spectrochimica Acta Part A, vol. 61, Issue 10, Aug. 2005, p. 2324-2334.

Thomspon, et al., "Combined Remote LIBS and Raman Spectroscopy Measurements," Lunar and Planetary Science Conference, XXXVI, #1517, Houston, Texas, Mar. 14-18, 2005. (Available at: http://www.lpi.usra.edu/meetings/lpsc2005/pdf/1517.pdf), Last Accessed Sep. 23, 2008.

Hubble, et al., "A Combined Remote LIBS and Raman Spectroscopic Study of Minerals," Lunar and Planetary Science Conference, XXXIII, #1935, Houston, Texas, Mar. 11-15, 2002. (Available at: http://www.lpi.usra.edu/meetings/lpsc2002/pdf/1935.pdf), Last Accessed Sep. 23, 2008.

* cited by examiner

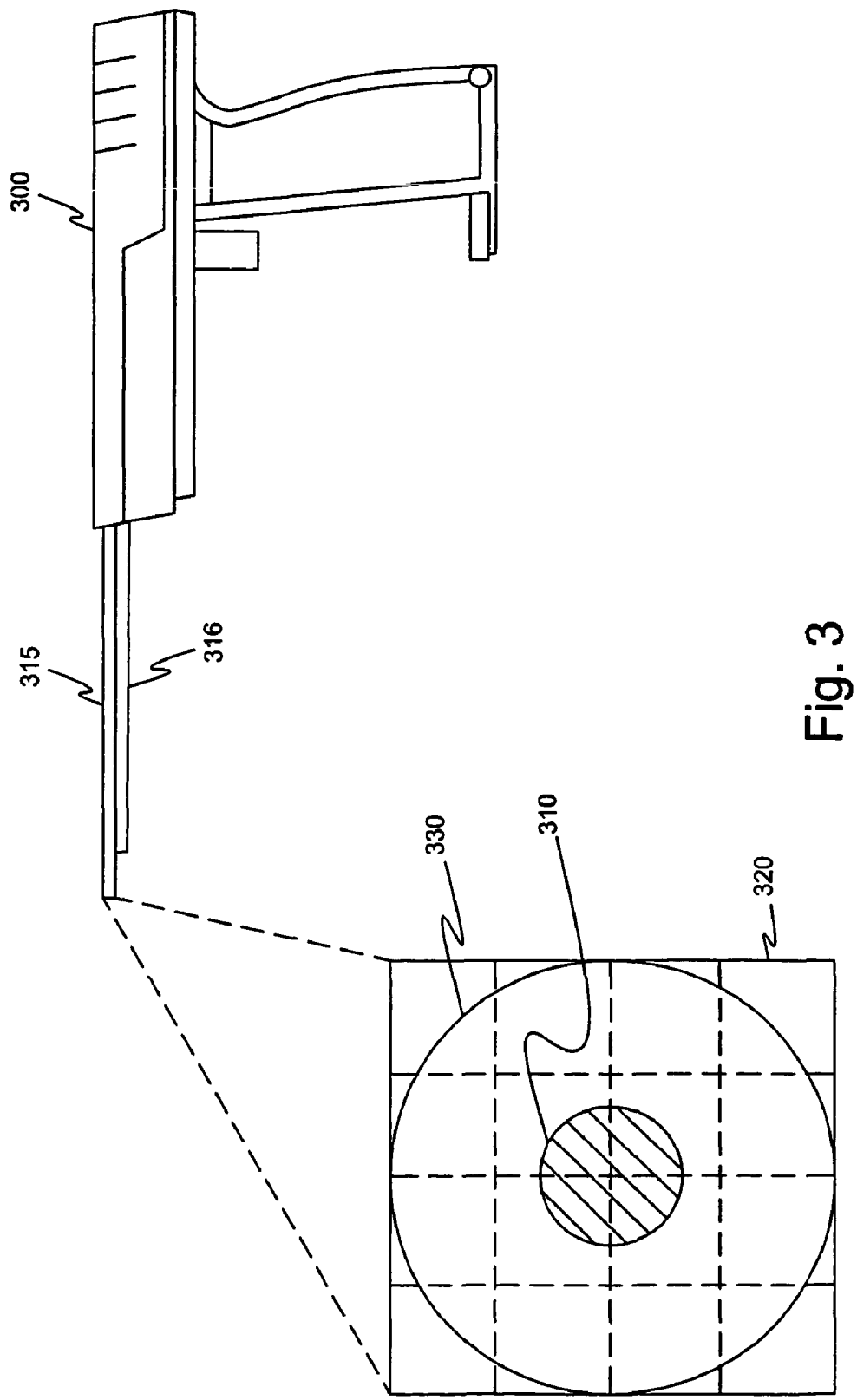

METHOD AND SYSTEM FOR COMBINED RAMAN AND LIBS DETECTION

The application claims priority to the filing-date of the Provisional Application No. 60/761,235, filed Jan. 23, 2006 (entitled: "Combined Raman and LIBS BioChem Detection System); Provisional Application No. 60/761,255, filed Jan. 23, 2006 (entitled: "End-to-End Performance Modeling of a ChemBio Raman Electrostatic Detector Identifier (CB-REDI) Reagentless Sensor System"); and Provisional Application No. 60/761,256, filed Jan. 23, 2006 (entitled: "Raman Detection of Waterborne Threats"), the disclosure of each provisional application is incorporated herein by reference in its entirety.

The instant application also references earlier filed patent application Ser. No. 11/351,333, filed Feb. 9, 2006 (entitled: "System and Method for the Deposition, Detection and Identification of threat Agents using a Phase Mask"), and assigned to the assignee of the instant application, the specification of which is incorporated herein in its entirety.

BACKGROUND

Deployment of threat agents poses significant threats to both human and economic health. The threat is compounded by a limited ability to detect deployment of the agents. Prior art detection strategies rely on separate instrumentation for detection and identification of the threat agent. Conventional means of detecting airborne matter include relatively non-specific optical and spectroscopic methods, including laser scattering and ultraviolet laser induced fluorescence (UV-LIF). Conventional means to identify a threat agent include wet chemical methods or spectroscopic methods. Reagent-based identification of biological threat agents includes methods such as specific antibodies, genetic markers and propagation in culture. While highly specific, these identification methods are time-consuming, labor-intensive and costly.

Spectroscopic means, for identification, provide an alternative to reagent-based identification methods and include mass spectrometry, infrared spectroscopy, Raman spectroscopy, laser induced breakdown spectroscopy (LIBS), and imaging spectrometry. Mass spectrometry is limited by sensitivity to background interference. Infrared spectroscopy exhibits low sensitivity. Raman spectroscopy is a good candidate for detection of threat agents based on its ability to provide a molecular "fingerprint" for materials with high specificity Raman spectroscopy can be implemented in several different configurations, including normal Raman spectroscopy, UV resonance Raman spectroscopy, surface enhanced Raman spectroscopy (SERS) and non-linear Raman spectroscopy.

While normal Raman spectroscopy has demonstrated adequate sensitivity and specificity for detection of airborne matter, other forms of Raman spectroscopy suffer from inadequate sensitivity, specificity or signature robustness. LIBS is also a good candidate for detection of threat agents based on its ability provide an elemental "fingerprint" for materials with high sensitivity. Prior art imaging spectroscopy is limited by the need to switch from a broadband light source, for optical imaging, to a substantially monochromatic light source for spectroscopic imaging. This results in a signification delay and inefficiency during detection during which the sample may degrade.

In order to improve the overall sensitivity and specificity of a fieldable threat detection, the invention combines two well known and proven techniques, Raman and LIES, into a system optimized for threat detection. Both individual methods have demonstrated the ability to detect threats in point sensing, proximity sensing and standoff sensing configurations. Improved overall detection performance can be realized through appropriate chemometric spectral processing algorithms applied to the fused data of the two orthogonal techniques. By combining Raman and LIBS techniques, threat detection performance can be improved relative to the individual techniques acting alone.

SUMMARY

In one embodiment, the disclosure relates to a method for interrogating a sample. The method comprising: illuminating a first region of the sample with a first illumination pattern to obtain a plurality of first sample photons; illuminating a second region of the sample with a second illumination pattern to obtain a plurality of second sample photons; processing the plurality of first sample photons to obtain a characteristic atomic emission of the first region and processing the plurality of second sample photons to obtain a Raman spectrum; and identifying the sample through at least one of the characteristic atomic emission of the first region or the Raman spectrum of the second region of the sample.

In another embodiment, the disclosure relates to a method for interrogation of a sample, comprising: (a) identifying a first region and a second region of the sample; (b) identifying a constituent of the first region by analyzing a characteristic atomic-emission from the first region; and (c) obtaining a spatially accurate wavelength resolved image of the second region of the sample. Steps (a)-(c) can be repeated for an alternative first and second regions of the sample.

In still another embodiment, the disclosure relates to an identification system comprising: a first illumination source for providing a first plurality of photons to a first region of the sample and a second illumination source for providing a second plurality of photons to a second region of the sample; a collector for receiving sample photons from each of the first and the second regions, the photons received from the first region providing a characteristic atomic emission of the sample and the photons received from the second region defining a Raman spectrum for the sample; a processor for processing sample photons from the first region and the second region; and a display for displaying at least one of a chemical identification or a spectral representation of the first or the second regions of the sample.

BRIEF DESCRIPTION OF THE DRAWINGS

These and other embodiments of the disclosure will be discussed in relation to the following non-limiting and exemplary drawings, in which:

FIG. 3 is a schematic representation for an apparatus according to one embodiment of the disclosure;

DETAILED DESCRIPTION

Raman spectroscopy has emerged as an attractive candidate for reagentless detection technology and shows significant capabilities in controlled studies for field detection of both chemical, Radiological, nuclear, and explosive (CBRNE) biological agents. Specifically, Raman sensing is being exploited for chemical surface contamination, on-the-move detection, white powder identification using handheld Raman sensors, and for waterborne pathogen detection. However, For identifying certain bio-chemical agents, Raman detection fails to provide a conclusive determination.

Laser Induced Breakdown Spectroscopy (LIBS) is a type of atomic emission spectroscopy which uses a highly energetic laser pulse as the excitation source. Because all substances emit light when excited to sufficiently high temperatures, LIES can detect all elements, limited only by the power of the laser as well as the sensitivity and wavelength range of the spectrograph and the detector. The development of the broadband, high-resolution spectrometer, along with advanced chemometric approaches, has enabled LIBS to demonstrate real-time detection and discrimination of hazardous chemical, biological and explosive (CBRNE) materials. Operationally, LIES is very similar to arc/spark emission spectroscopy. The laser pulses delivered to the sample can be mildly destructive of the sample. However, the laser pulses can be directed to a specific region of the sample, making the surrounding sample material available for Raman sampling.

Thus, according to one embodiment of the disclosure an integrated detection system synergistically combines Raman detection mode with LIBS technologies to provide an integrated and efficient detection system. The combined Raman/LIBS sensory system can provide reagentless sensing technology for the detection and identification of chemical or biological agents. In another embodiment, the disclosure relates to a structured illumination method and apparatus.

Figure 1:
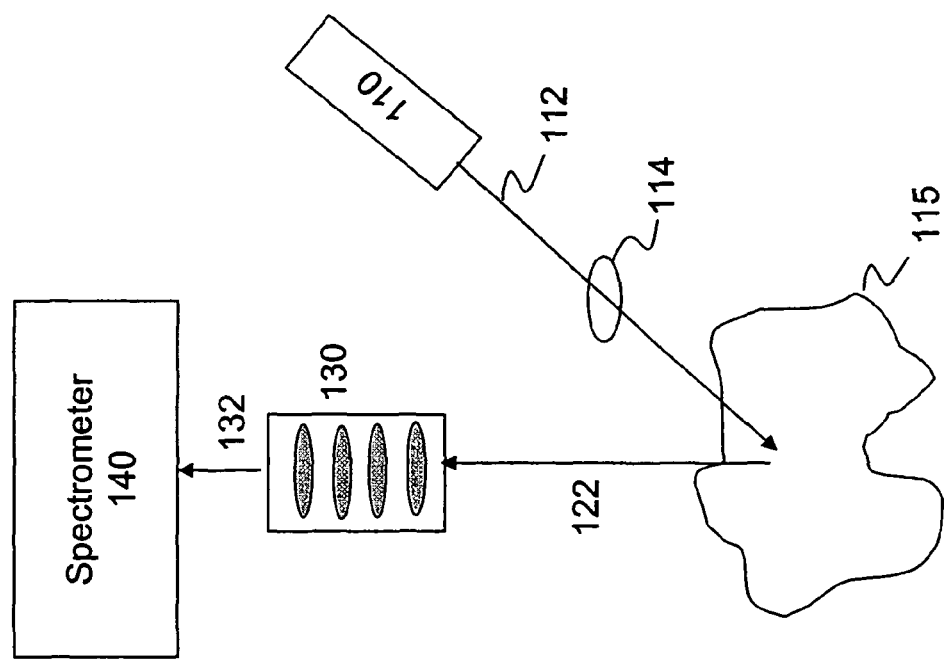
FIG. 1 is a spectroscopy system according to one embodiment of the disclosure.

FIG. 1 is a spectroscopy system according to one embodiment of the disclosure. The system shown in FIG. 1 can be configured as a handheld device, point detection device, or a standoff detector device. The spectroscopy device of FIG. 1 can be used, for example, to simultaneously obtain spectroscopic images of a sample. The images can define different spectroscopic modes such as laser scattering, ultraviolet laser induced fluorescence (UV-LIF) and laser induced breakdown spectroscopy (LIBS). In FIG. 1, illumination source 110 provides a plurality of illuminating photons to sample 115. Optical device 114 may include one or more light gathering optics and it may optionally be used to focus, filter or direct illumination photons 112 to sample 115. Once illuminated, sample photons 122 can be collected by gathering optics 130 and directed to spectrometer 140. Spectrometer 140 can be configured to receive and process different types of spectra simultaneously. In one embodiment, spectrometer 140 receives and processes sample photons for simultaneously forming Raman and LIBS spectra for sample 115. In one embodiment, first sample photons are processed to obtain Raman spectra for the sample and then second sample photons are processed to obtain LIBS spectra for the sample.

The exemplary system of FIG. 1 can include a fiber array spectral translator ("FAST"). For example, transmission line 132 can comprise a fiber bundle such that a first end of the fiber bundle optically communicates with gathering optics 130 while the second end of the fiber bundle communicates with spectrometer 140. The first end of the fiber bundle can comprise of a two dimensional non-linear array of fiber bundles. The second end of the fiber bundle can comprise of curvilinear array of fibers wherein curvilinear may include a straight line as well as a curved line configuration. In an alternative embodiment, the system of FIG. 1 may additionally include an optical filter such as Liquid Crystal Tunable Filter (LCTF), Monolithic Crystal Filter (MCF) or an Acousto-Optic Tunable Filter (AOTF). The system of FIG. 1 may also be configured for use with Computed Tomography Imaging Spectroscopy (CTIS).

Figure 2A:
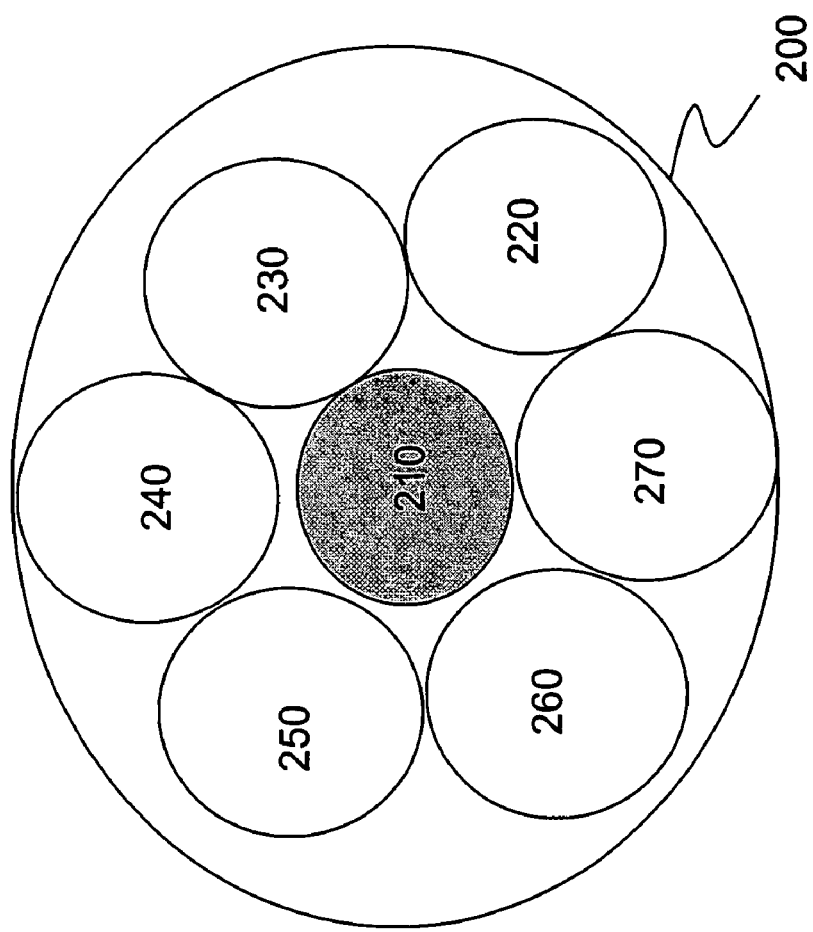
FIG. 2A is an exemplary structured illumination configuration according to one embodiment of the disclosure.

FIG. 2A is an exemplary structured illumination configuration according to one embodiment of the disclosure. In FIG. 2A, illumination circle 200 represents an illuminated area of a sample. Area 200 can be illuminated with photons having a first wavelength and region 210 can be illuminated with photons having a second wavelength. Thus, area 200 can be illuminated with photons of a first wavelength to obtain a Raman spectra for area 200. Thereafter, region 210 can be illuminated with photons of a second wavelength to obtain LIBS spectra for region 210. The sample can be illuminated to obtain Raman spectra before LIBS. Alternatively, the sample can be illuminated to obtain LIBS spectra before Raman. In still another embodiment, the annulus area between rings 200 and 210 can be used to obtain LIES spectra and region 210 can be used for obtaining Raman spectra.

In an embodiment, area 200 and region 210 cane be illuminated simultaneously with photons of different wavelength. Photons of a first wavelength can illuminate the entire area 200 (or the annulus region between area 200 and region 210), and photons of a second wavelength can illuminate region 210. Raman spectra can be collected from regions 220-270, while LIBS spectra is simultaneously collected from region 210. In the even that the region 210 is illuminated simultaneously with photons of the first and second wavelength, optical filters and detectors can be used to remove unwanted sample photons.

In another embodiment of FIG. 2A, each of regions 220-270 shows a region of the sample from which Raman-scattered photons may be collected. Region 210 can represent a region for which LIBS can be implemented to obtain an atomic signature of the sample under study. The atomic signature of the sample can define the chemical identify of the sample at region 210. Regions 210-270 can have the shape of a circle, an ellipse, a rectangle, a square, a hexagon or any other shape. The combined analysis is advantageous in that it provides a significant synergistic performance of Raman and LIBS. That is, the structured illumination provides the specificity of Raman molecular spectroscopy along with LIBS elemental spectroscopy.

The structured illumination configuration of FIG. 2A can reflect an arrangement of the illumination sources (not shown). For example, the illumination configuration can comprise a first laser source for illuminating the entire region with photons of a first frequency and a second laser source for illuminating region 210 with photons of a second frequency. The arrangement of the first and second laser sources can be adapted to provide the structured illumination of FIGS. 2A-2C or variations thereof.

As stated, area 200 and region 210 can be illuminated simultaneously or sequentially. In one embodiment, area 200 is first illuminated with photons of the first wavelength. Sample photons can then be collected from each of the regions 220-270. Next, region 210 can be illuminated with photons of a second wavelength and sample photons can be collected therefrom. In an embodiment where the first wavelength provides a Raman spectrum and the second wavelength provides laser induced breakdown spectroscopy of the sample, collecting Raman photons from the sample before implementing laser induced breakdown spectroscopy enables Raman detection before a region of the sample (e.g., region 210) may be partially destroyed by LIBS.

In another embodiment, area 200 is illuminated substantially simultaneously with region 210. That is, photons of the first wavelength and photons of the second wavelength are directed to the sample at substantially the same time to independently collect sample photons from area 200 and region 210. According to this embodiment, the detection and analysis of the sample can be implemented simultaneously. Such implementation can be particularly beneficial for large samples where a sample is divided into a number of segments and each segment is analyzed independently of the remaining segments.

Figure 2B:
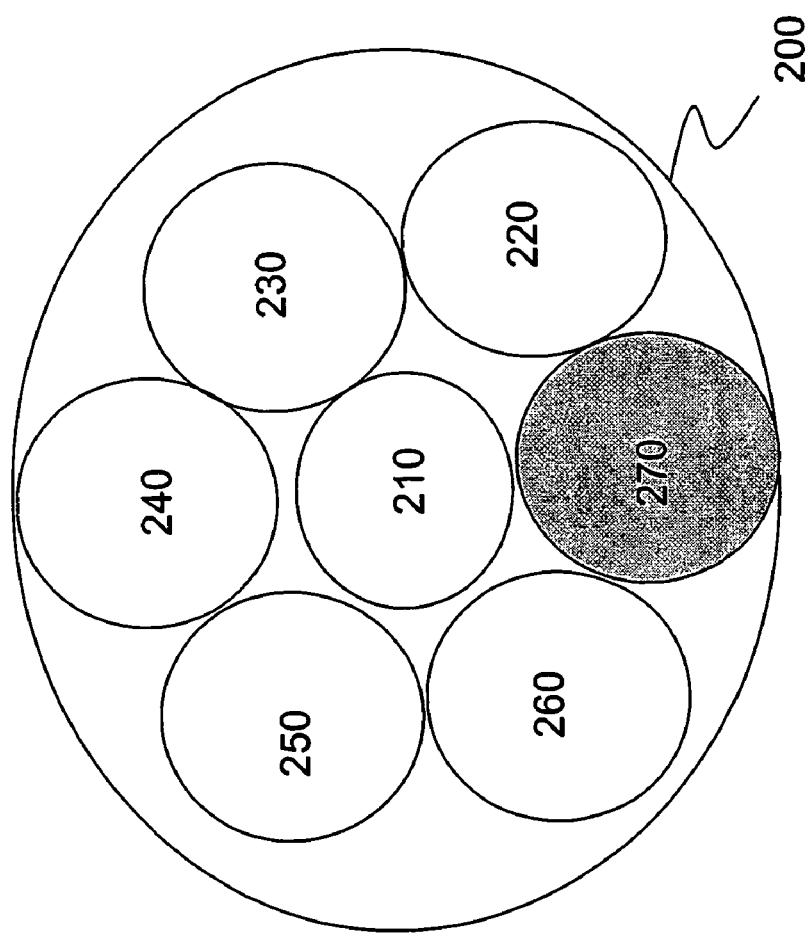
FIG. 2B is another exemplary structured illumination configuration according to one embodiment of the disclosure.

FIG. 2B is another exemplary structured illumination configuration according to an embodiment of the disclosure. In the structured illumination configuration of FIG. 2B, the area 200 is illuminated with photons of a first wavelength and region 270 can be illuminated with photons of a second wavelength. The photons of the first wavelength can elicit Raman spectra for regions 210-260 while sample photons collected from region 270 can identify the sample through LIBS. The illumination of area 200 and region 270 can overlap. That is, both area 200 and region 270 can be illuminated simultaneously.

Figure 2C:
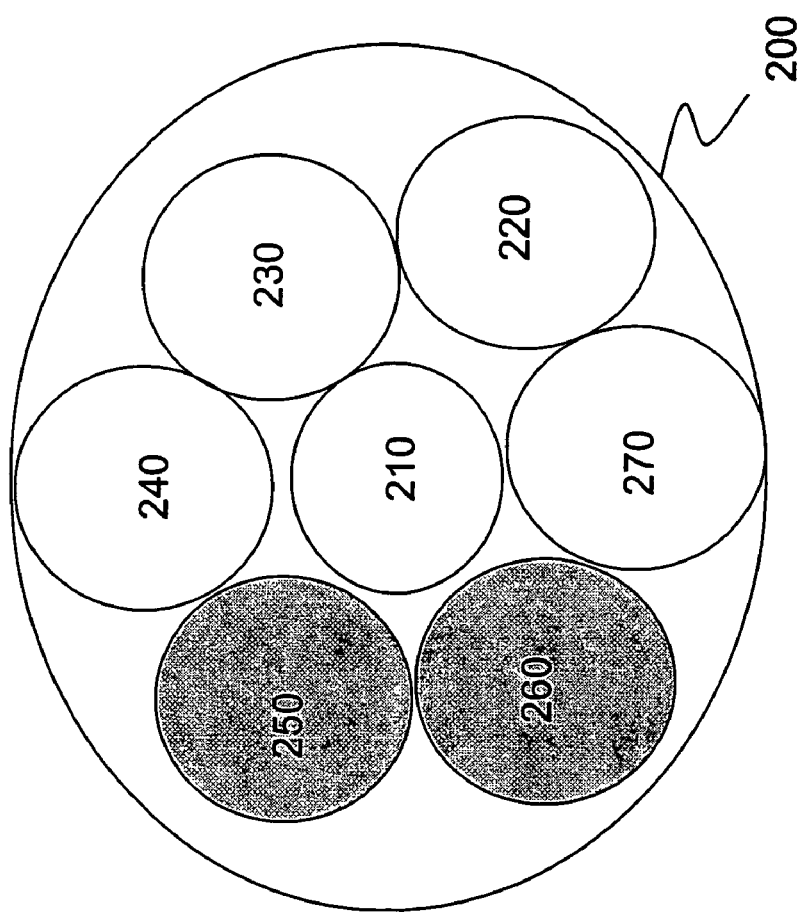
FIG. 2C is yet another exemplary structured illumination configuration according to one embodiment of the disclosure.

Similarly, FIG. 2C is yet another exemplary structured illumination configuration according to one embodiment of the disclosure. In FIG. 2C, area 200 is illuminated with photons having a first wavelength to collect sample photons from regions 210, 220, 230, 240 and 270. Photons having a second wavelength illuminate different regions of the sample to provide sample photons from regions 250 and 260. The sample photons from different regions 210-270 can be used to identify the sample. For example, if Raman spectra is collected from regions 210, 220, 230, 240 and 270 and regions 250 and 260 are used for LIBS, the sample under study can be identified by its Raman spectra and its atomic emission.

FIG. 3 is a schematic representation for an apparatus according to one embodiment of the disclosure. FIG. 3 can provide illumination source as well as the collection optics and the spectroscopy device. More specifically, FIG. 3 provides integrated handheld device 300 for sample detection and analysis. Handheld device 300 can include illumination source 315 and collection point 316. The illumination source can be integrated with the handheld device or it can be provided as a nozzle attachment. In one embodiment of the disclosure, nozzle 316 can be configured to collect sample photons. Further, the illumination source can be configured to provide structured illumination for sample 320. In FIG. 3, sample 320 is illuminated with photons of a first wavelength at region 310 and photons of a second wavelength at region 330. Regions 310 and 330 can overlap as shown. Photons collected from region 310 can provide laser induced breakdown spectroscopy and photons collected from the remainder of region 330 can be used to construct a Raman spectra for the sample. Both regions 310 and 330 of sample 320 can be illuminated simultaneously by an illumination source configured to provide photons of a first wavelength to region 330 and photons of a second wavelength to region 310. The illumination source may comprise two laser illumination devices concentrically positioned to form an annulus and to provide the illumination shown in FIG. 3.

Figure 4B:
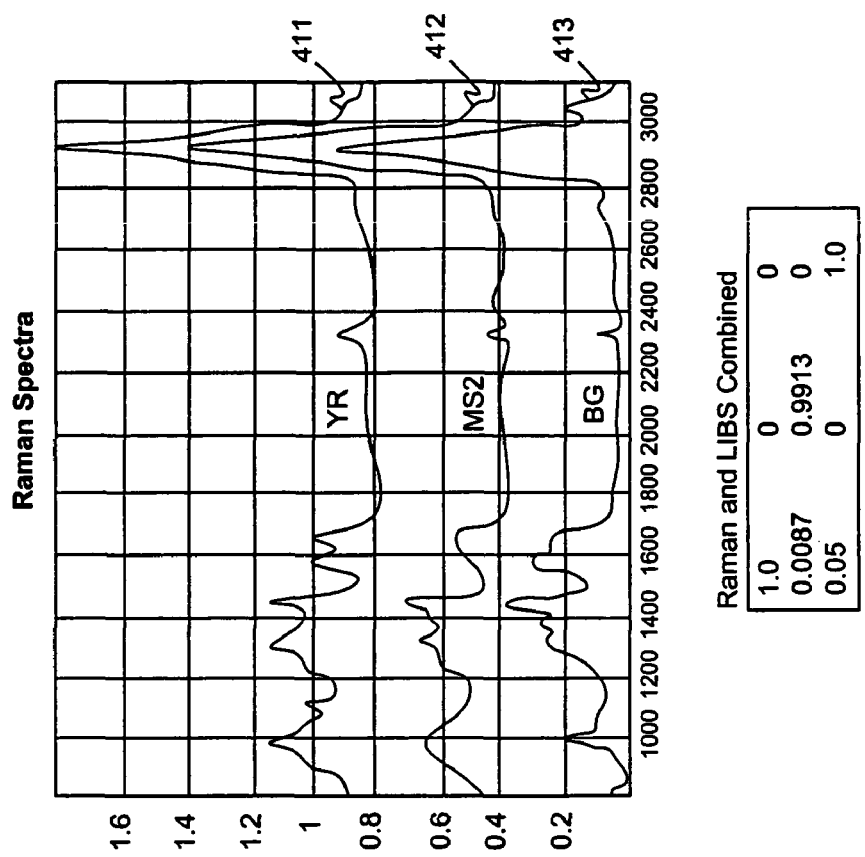
FIGS. 4A and 4B respectively show LIBS and Raman spectra of a sample.
Figure 4A:
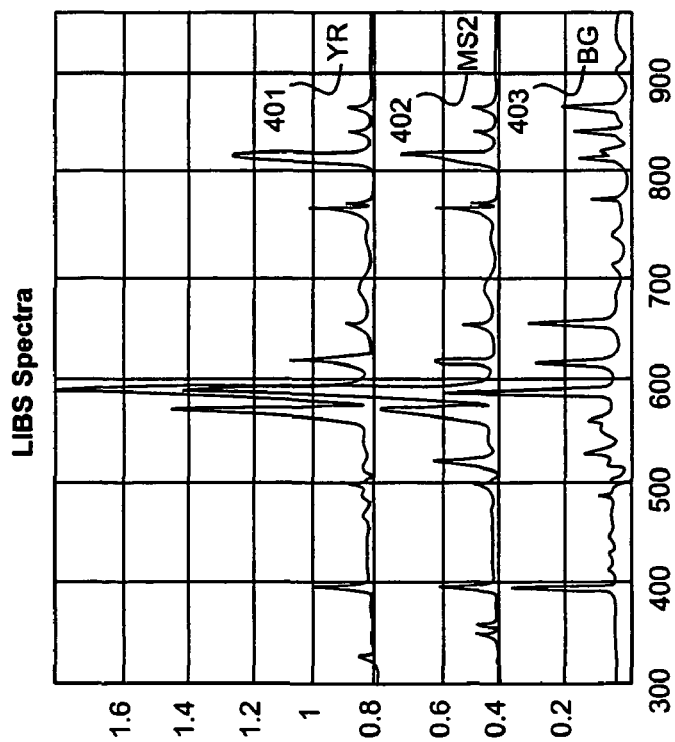

FIG. 4A shows LIBS spectra collected from a sample. Specifically, FIG. 4A shows the presence of *Yersinia Rhodei* (YR) 401, MS2 bacteriophage virus 402, and *bacillus globigii* (BG) 403 as indicated by each of their respective spectra. FIG. 4B shows Raman spectra collected from the sample of FIG. 4A. The Raman spectrum for each of YR 411, MS2 virus 412 and BG 413 are shown. In addition, at the bottom of FIGS. 4A and 4B, confusion matrices are shown for each of the Raman, LIBS and combined Raman/LIBS sensing, respectively, of YR, MS2 and BG.

A confusion matrix quantifies the degree or relatedness of spectra within specific classes contained in a training dataset, as well as providing an estimate of the degree of specificity inherent in the analysis and dominant sources of interference between classes (crosstalk). In this example, the classes are comprised of Yr, MS2 and BG. The confusion matrix is calculated by organizing the species-level Raman spectra into three unique classes. PCA analysis was performed and the first 10 PCs were employed to construct a supervised Mahalanobis distance model boundary classifier for each of the 3 biological classes. The classifier consisted of a mean spectrum, covariance matrix, and an ellipsoidal boundary. Each spectrum, as a point in the N=10 dimensional PC dataspace, was compared with the ellipsoidal boundaries. The minimum distance classification rule (nearest neighbor approach) was used whereby a spectrum was deemed a member of a particular class (ellipsoidal boundary) if its distance from that class was less than its distance from all other classes. Each row in the confusion matrix is the biological identity of the spectra, and the column entries show how the Mahalanobis distance based classifier classified the spectra. A perfect classifier has entries only along the diagonal. Confusion matrices are a predictor of the specificity of an identification algorithm in which the diagonal elements are correlated with the probabilities of correct identification ($P_d$) for each of the species, while the off-diagonal elements correlate with the probability of false positive ($P_{fp}$). The confusion matrix can change depending on the spectral range and number of principal components employed to construct the MD model. In the confusion matrices of FIGS. 4A and 4B, it is evident that there is a reduction in probability of false positive detections in the Raman/LIBS combined approach relative to Raman or LIBS operating alone.

Figure 5:
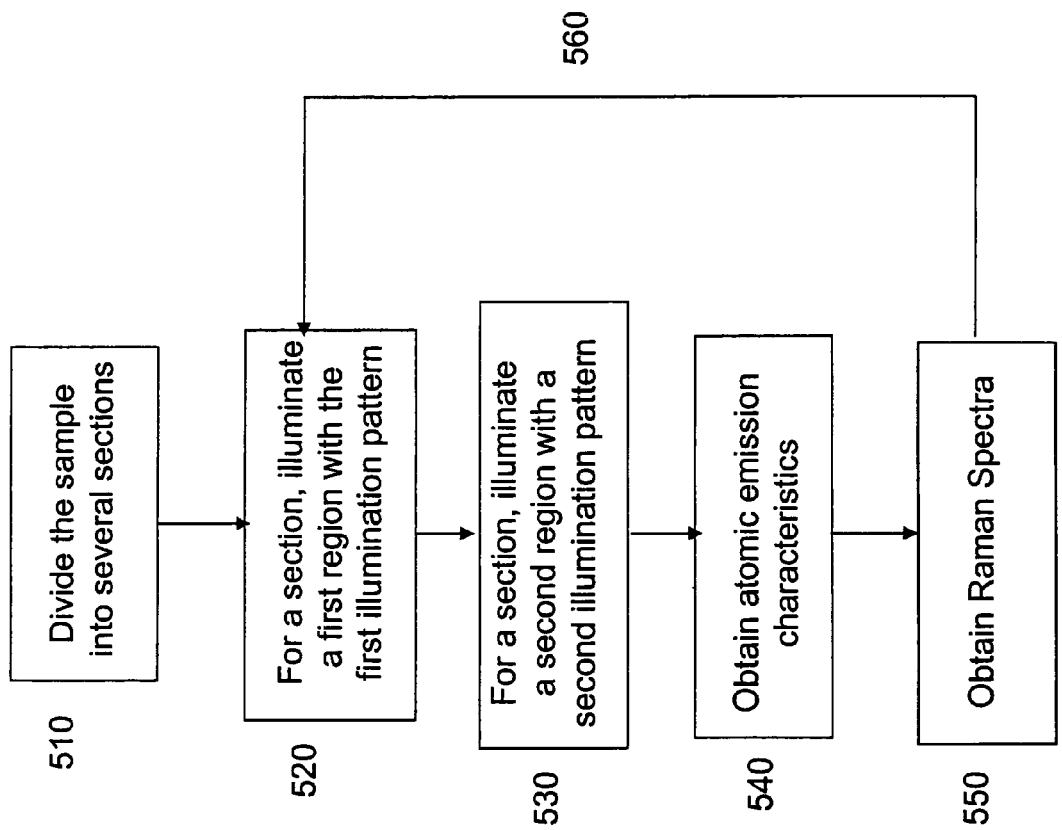
FIG. 5 is an exemplary algorithm according to an embodiment of the disclosure.

FIG. 5 is an exemplary algorithm according to an embodiment of the disclosure. The exemplary algorithm of FIG. 5 can define a software or a firmware. The exemplary algorithm of FIG. 5 can be used with the system of FIG. 1 or apparatus of FIG. 3. In the optional step 510, the sample is visually divided into several sections. For example, the sample can be visually divided into a grid and each grid (section) can be analyzed independently. In step 520, a selected section of the sample is illuminated with photons of a first wavelength to obtain a first sample photons. The first sample photons can be used for Raman spectroscopy. In step 530, the selected section is illuminated with photons of a second wavelength to obtain second sample photons. The second sample photons can be used for laser induced breakdown spectroscopy. Steps 520 and 530 can be implemented substantially simultaneously or sequentially.

The first sample photons can be used to obtain the Raman spectra for the sample at step 540. The information can also be used to obtain a spatially accurate, wavelength resolved image of the section under study. That is, the spatially accurate, wavelength resolved image of the sample can be obtained for the Raman spectra as well as the LIBS spectra. A spatially accurate wavelength-resolved image is an image of a sample that is formed from multiple "frames" wherein each frame has plural spatial dimensions and is created from photons of a particular wavelength (or wave number) or from photons in a particular wavelength band (or wave number band) so that the frames may be combined to form a complete image across all wavelengths (wave numbers) of interest. The second sample photons can be used to obtain the atomic characteristic of the sample in step 550. The results from steps 540 and 550 can be used to section of the sample under study. Steps 520-550 can be repeated to study different visual sections of the sample as shown by arrow 560.

In another embodiment, the disclosure relates to a method and apparatus for detecting and identifying chemical or biological agents, including aerosols and low vapor pressure chemicals by using electrostatic collection devices with hyperspectral Raman imaging devices. The detection processes can be implemented without using reagents. An exemplary system can include: (1) an electrostatic collector for particulate collection and low vapor pressure chemical aerosol collection; (2) an autonomous surface deposition subsystem providing concentrated threat agents; (3) a hyperspectral Raman imaging sensor optionally having a low-power imaging sensor, a digital camera for sample focusing and an imaging spectrometer for generating spatially-resolved Raman spectra with sampling statistics necessary to differentiate target from background; and (4) a decision making algorithm for threat agent identification in the presence of clutter or background noise.

In another embodiment, the disclosure relates to a reagent-less detector for biological threats in water. Biological sample variables include: genetic near neighbors, strain, serotype, growth conditions and viability. To identify the substance, Mahalanobis Distance correlation metric can be used. In a method according to one embodiment, detection and identification of waterborne threats without using reagents comprises the following process steps: sample collection; agent pre-concentration; detection and identification; automated decision making; and data management. The agent pre-concentration step can include: sample collection, water-contaminant pre-concentration, and sample deposition. The detection and identification step can include optical microscopy as well as Raman spectroscopy and imaging. The automated decision making step may include one or more algorithm for analyzing the spectroscopy results and identifying the sample.

The above description is not intended and should not be construed to be limited to the examples given but should be granted the full breadth of protection afforded by the appended claims and equivalents thereto. Although the disclosure is described using illustrative embodiments provided herein, it should be understood that the principles of the disclosure are not limited thereto and may include modification thereto and permutations thereof.

What is claimed is:

1. A method for interrogating a sample, comprising:
   illuminating a first region of the sample with a first illumination pattern to obtain a plurality of first sample photons;
   illuminating a second region of the sample with a second illumination pattern to obtain a plurality of second sample photons;
   filtering the plurality of second sample photons through an electronically controlled tunable filter;
   processing the plurality of first sample photons to obtain a characteristic atomic emission of the first region and processing the plurality of second sample photons to obtain a Raman spectrum; and
   identifying the sample through at least one of the characteristic atomic emission of the first region or the Raman spectrum of the second region of the sample.

2. The method of claim 1, wherein the first illumination pattern defines one of a circle, a square, a rectangle or an ellipse.

3. The method of claim 1, wherein the second illumination pattern defines one of a circle, a square, a rectangle, an ellipse or an annulus.

4. The method of claim 1, wherein the first region and the second region partially overlap.

5. The method of claim 1, wherein the step of illuminating the first region further comprises illuminating the second region with laser energy sufficient for Raman spectroscopy.

6. The method of claim 1, wherein the step of illuminating the second region further comprises illuminating the first region with laser energy sufficient for atomic spectroscopy or with laser energy sufficient for induced breakdown spectroscopy.

7. The method of claim 1, wherein the steps of illuminating the first region and illuminating the second region are implemented sequentially.

8. The method of claim 1, wherein the steps of illuminating the first region and illuminating the second region are implemented substantially simultaneously.

9. A method for interrogation of a sample, comprising:
   (a) identifying a first region and a second region of the sample;
   (b) obtaining a spatially accurate wavelength resolved image of the second region of the sample, wherein said obtaining comprises:
   illuminating the second region of the sample to obtain a plurality of sample photons from said second region, and
   filtering the plurality of sample photons from said second region though an electronically controlled tunable filter; and
   (c) identifying a constituent of the first region by analyzing a characteristic atomic-emission from the first region.

10. The method of claim 9, further comprising: (d) repeating steps (a)-(c) for an alternative first region and an alternative second region of the sample.

11. The method of claim 9, wherein the first region and the second region overlap.

12. The method of claim 9, wherein the first region and the second region do not overlap.

13. The method of claim 9, wherein step (c) further comprises:
   (c)(1) illuminating the sample to produce a plurality of laser induced break down photons; and
   (c)(2) collecting the plurality of photons.

14. The method of claim 9, wherein step (b) further comprises:
   (b)(1) illuminating the sample to produce a plurality of sample-scattered photons;
   (b)(2) collecting the plurality of sample-scattered photons; and
   (b)(3) forming a Raman image of the second region from the collected photons.

15. The method of claim 9, further comprising implementing steps (b) and (c) substantially simultaneously.

16. The method of claim 9, further comprising implementing steps (b) and (c) sequentially.

17. The method of claim 9, further comprising obtaining a spatially accurate wavelength resolved image of the first region of the sample.

18. An identification system comprising:
   a first illumination source for providing a first plurality of illumination photons to a first region of a sample to thereby form a first plurality of sample photons, and a second illumination source for providing a second plurality of illumination photons to a second region of the sample to thereby form a second plurality of sample photons;
   an electronically controlled tunable filter for filtering at least one of said first plurality of sample photons and said second plurality of sample photons;

a collector for receiving said first and second plurality of sample photons and providing first and second signals respectively therefrom, wherein said first plurality of photons is representative of a Raman spectrum for the sample and said second plurality of photons is representative of a characteristic atomic emission of the sample;

a processor for processing said first and second signals; and a display for displaying at least one of a chemical identification or a spectral representation of the first or the second regions of the sample.

19. The system of claim 18, wherein the identification system is a handheld device.

20. The system of claim 18, wherein the first plurality of photons have an energy level sufficient for Raman spectroscopy.

21. The system of claim 18, wherein the second plurality of photons have an energy level sufficient for laser induced breakdown spectroscopy.

22. The system of claim 18, wherein the identification system substantially simultaneously illuminates the first and the second regions of the sample.

23. The system of claim 18, wherein the identification system sequentially illuminates the first and the second regions of the sample.

24. The system of claim 18, wherein the collector further comprises an optical collection train and a detection system.

25. The system of claim 24, wherein the detection system is one of a charge-coupled device or a CMOS detector.

26. The system of claim 18, wherein the first region and the second region overlap.

27. The system of claim 18, further comprising a fiber array spectral translator for communicating sample photons from the collector to a spectrometer.

28. The method of claim 1 further comprising the step of obtaining a spatially accurate wavelength resolved image of the second region.

29. The method of claim 14 further comprising the step of filtering the plurality of sample-scattered photons through an electronically controlled tunable filter.

30. A method for interrogating a sample, comprising:
   illuminating a first region of the sample with a first illumination pattern to obtain a first plurality of sample photons;
   illuminating a second region of the sample with a second illumination pattern to obtain a second plurality of sample photons;
   passing at least one of the first plurality of sample photons and the second plurality of sample photons through a fiber array spectral translator;
   passing at least one of the first plurality of sample photons and the second plurality of sample photons through a tunable filter;
   processing the first plurality of sample photons to obtain a characteristic atomic emission of the first region and processing the plurality of sample photons to obtain a Raman spectrum; and
   identifying the sample though at least one of the characteristic atomic emission of the first region or the Raman spectrum of the second region of the sample.

31. A method for interrogation of a sample, comprising:
   (a) identifying a first region of the sample and a second region of the sample;
   (b) obtaining a spatially accurate wavelength resolved image of the second region of the sample, wherein said obtaining comprises passing a plurality of sample photons from said second region through an electronically tunable filter; and
   (c) identifying a constituent of the first region by analyzing a characteristic atomic-emission from the first region.

32. A method for interrogation of a sample, comprising:
   (a) identifying a first region of the sample and a second region of the sample;
   (b) obtaining a spatially accurate wavelength resolved image of the second region of the sample, wherein said obtaining comprises
   passing a plurality of sample photons from said second region through a fiber array spectral translator, and
   passing the plurality of sample photons from said second region through a tunable filter; and
   (c) identifying a constituent of the first region by analyzing a characteristic atomic-emission from the first region.

33. An identification system comprising:
   a first illumination source for providing a first plurality of illumination photons to a first region of a sample to thereby form a first plurality of sample photons, and a second illumination source for providing a second plurality of photons to a second region of the sample to thereby form a second plurality of sample photons;
   a fiber array spectral translator for passing at least one of said first plurality of sample photons and said second plurality of sample photons to a collector;
   a tunable filter for passing at least one of said first plurality of sample photons and said second plurality of sample photons;
   said collector for receiving said first plurality of sample photons and said second plurality of sample photons and providing first and second signals respectively therefrom, wherein said first plurality of sample photons is representative of a Raman spectrum for the sample and said second plurality of sample photons is representative of a characteristic atomic emission of the sample;
   a processor for processing said first and second signals; and
   a display for displaying at least one of chemical identification or a spectral representation of the first or the second regions of the sample.

* * * * *